(12) United States Patent
Cohn

(10) Patent No.: US 9,676,004 B2
(45) Date of Patent: Jun. 13, 2017

(54) SORTING SYSTEM

(71) Applicant: Avi Cohn, Underwood, WA (US)

(72) Inventor: Avi Cohn, Underwood, WA (US)

( * ) Notice: Subject to any disclaimer, the term of this patent is extended or adjusted under 35 U.S.C. 154(b) by 0 days.

(21) Appl. No.: 14/934,638

(22) Filed: Nov. 6, 2015

(65) Prior Publication Data

US 2016/0207071 A1    Jul. 21, 2016

Related U.S. Application Data

(60) Provisional application No. 62/103,962, filed on Jan. 15, 2015.

(51) Int. Cl.
| | | |
|---|---|---|
| *B07C 5/342* | (2006.01) | |
| *G01N 21/25* | (2006.01) | |
| *G01N 21/85* | (2006.01) | |
| *G01N 21/89* | (2006.01) | |
| *G01N 21/17* | (2006.01) | |
| *G01N 21/84* | (2006.01) | |

(52) U.S. Cl.
CPC ............ *B07C 5/342* (2013.01); *B07C 5/3425* (2013.01); *G01N 21/251* (2013.01); *G01N 21/85* (2013.01); *G01N 21/8901* (2013.01); *G01N 2021/1776* (2013.01); *G01N 2021/845* (2013.01); *G01N 2021/8592* (2013.01)

(58) Field of Classification Search
CPC ......... B07C 5/10; B07C 5/342; B07C 5/3422; B07C 5/3425; G01N 21/00; G01N 21/251; G01N 21/85; G01N 21/8901; G01N 2021/1776; G01N 2021/845; G01N 2021/8592; G01J 3/46; G06T 2207/10024
USPC .............. 209/576, 577, 580, 581, 587, 939; 382/162–167

See application file for complete search history.

(56) References Cited

U.S. PATENT DOCUMENTS

| | | |
|---|---|---|
| 4,530,434 A | 7/1985 | Wowczuk |
| 4,863,041 A | 9/1989 | Bailey |
| 5,339,963 A | 8/1994 | Tao |
| 5,432,545 A | 7/1995 | Connolly |
| 5,464,981 A | 11/1995 | Squyres |
| 5,533,628 A | 7/1996 | Tao |
| 5,813,542 A | 9/1998 | Cohn |
| 6,901,163 B1 | 5/2005 | Pearce et al. |
| 2011/0142366 A1* | 6/2011 | Young ............... G06T 3/4069 382/274 |
| 2011/0150331 A1* | 6/2011 | Young ............... G06T 3/4015 382/167 |

OTHER PUBLICATIONS

International Search Report and Written Opinion, dated Mar. 2, 2016, PCT International Patent App. No. PCT/US2015/059457, filed Nov. 6, 2015, 10 pgs.

* cited by examiner

*Primary Examiner* — Joseph C Rodriguez
*Assistant Examiner* — Kalyanavenkateshware Kumar
(74) *Attorney, Agent, or Firm* — Chernoff Vilhauer McClung & Stenzel, LLP

(57) ABSTRACT

A system for sorting products using an imaging device and an image processor.

13 Claims, 16 Drawing Sheets

SORTING SYSTEM

CROSS-REFERENCE TO RELATED APPLICATIONS

This application claims the benefit of U.S. Provisional App. No. 62/103,962, filed Jan. 15, 2015.

BACKGROUND OF THE INVENTION

The present invention relates to techniques for sorting objects by color.

Sorters with a single color camera, known as monochromatic sorters, detect light intensity variations reflected from objects being sorted. By varying the color of the lighting system, the camera can distinguish between a limited range of colors and shades within a color. However, a single color camera cannot effectively sort objects where the color variation between an object that should be accepted and an object that should be rejected is in more than one color domain.

Sorters with a multiple color camera system are used to sort objects which have colors in more than one color domain. Multiple color sorters traditionally use two or three different monochromatic cameras measuring the absolute light intensity reflectance from objects at two or three different colors, respectively. Red, green, and blue colors are frequently used because any color can be defined in terms of its red, green and blue color content.

What is desired, therefore, is a color sorting system based, at least in part, on the hue of an object so that operators may easily adjust the sorting criteria. The hue values should extend beyond the red to green color range in order to sort objects encompassing a broader color range. In addition, color saturation values and, in some cases, intensity values should preferably be used to enhance color recognition. The color sorting system should also be insensitive to light intensity variations. The speed and number of objects capable of being sorted should be maximized, while simultaneously minimizing errors from rotational movement of objects between cameras. Further, the sorting system should be capable of detecting small blemishes and enhancing the appropriate colors.

The foregoing and other objectives, features, and advantages of the invention may be more readily understood upon consideration of the following detailed description of the invention, taken in conjunction with the accompanying drawings.

DETAILED DESCRIPTION OF PREFERRED EMBODIMENT

Figure 1:
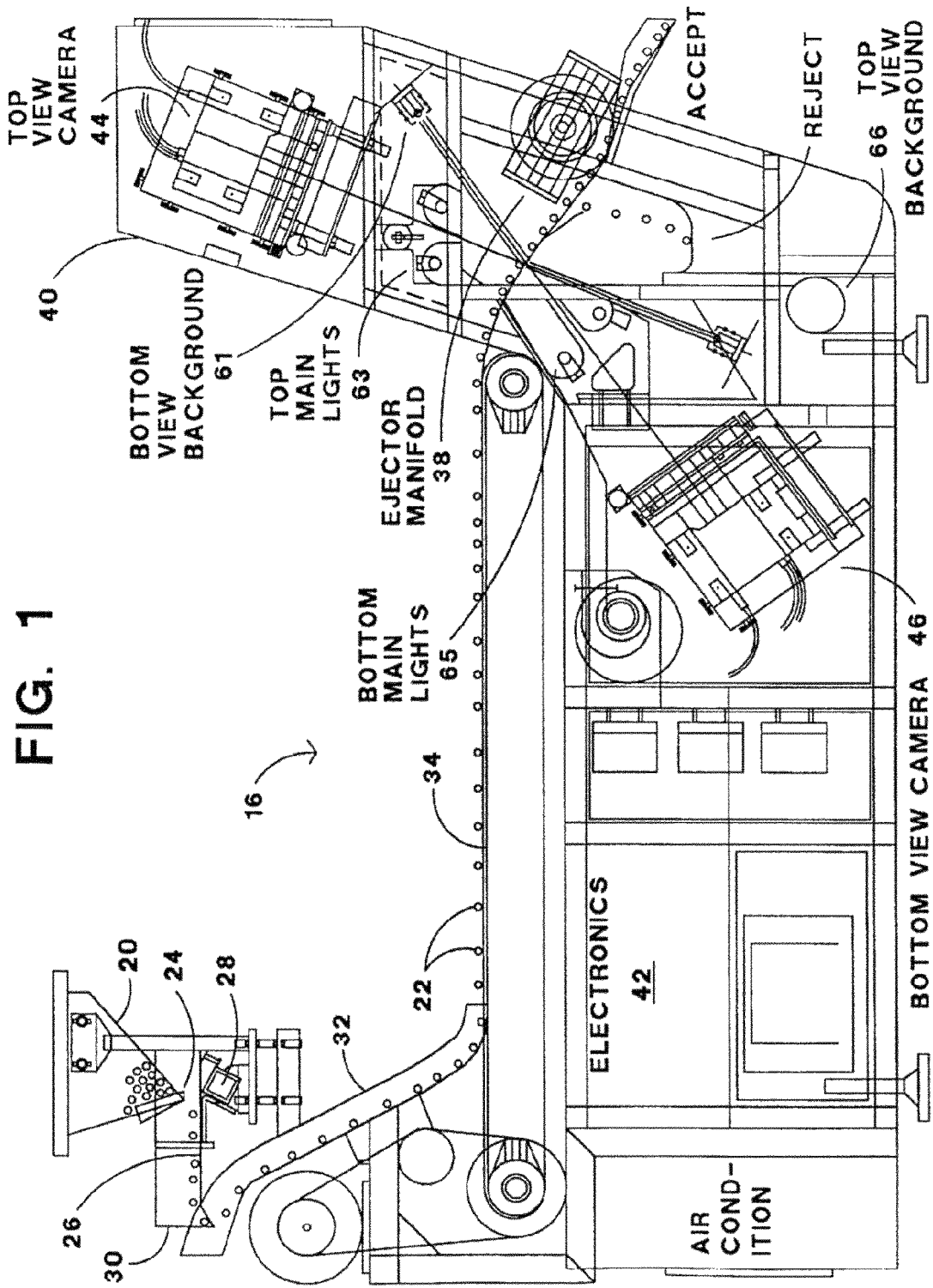
FIG. 1 is a side view of an exemplary color sorter system including a conveyor system, a camera section including two three-color cameras, electronics, and an ejector manifold.

Referring to FIG. 1, a sorting system 16 includes a hopper 20 that stores objects 22 to be sorted. Preferably the objects 22 are granular in nature, such as peanuts, rice, peas, etc. However, with appropriate modifications to the sorting system 16 other types of objects may be sorted, such as, for example, fruit and vegetables. The objects 22 are dispensed through a lower opening 24 in the hopper 20 onto a tray 26. A vibrator 28 vibrates the tray 26 separating the objects 22 from one another producing an even flow of objects 22 along the tray 26. The objects 22 fall off the end 30 of the tray 26 into an acceleration chute 32. The acceleration chute 32 increases the speed of objects 22 to approximately match the speed of a rotating continuous conveyor belt 34. The objects 22 are transported along the conveyor belt 34 and launched in a trajectory through a camera section 40. The camera section 40 senses a multiple color image of the objects 22 and produces color signals indicative of a plurality of colors. The color signals are transmitted to the electronics 42 to determine if the imaged objects 22 are acceptable or should be rejected. The electronics 42 controls a fluid nozzle ejector manifold 38 to sort the objects 22 into either an accept or reject bin by deflecting rejected objects from their normal trajectory. Alternatively, the conveyor system 16 could grade and sort the objects into one of multiple bins.

Figure 2:
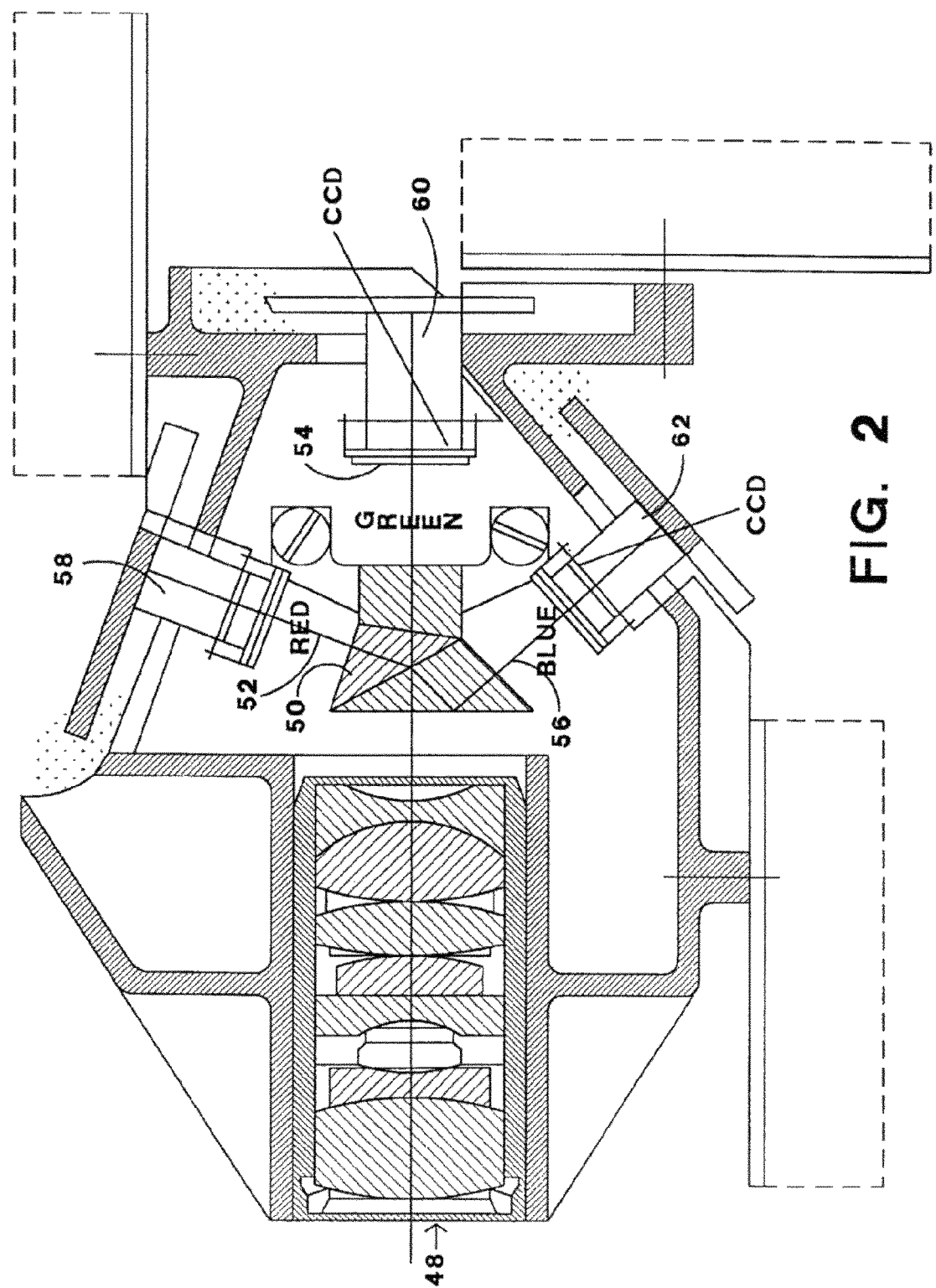
FIG. 2 is a sectional view of one of the three-color cameras of FIG. 1.

The camera section 40 includes a top view camera 44 and a bottom view camera 46, both of which are preferably identical, to simultaneously view two sides of the objects 22 across the view of the cameras 44 and 46. Referring to FIG. 2, the top view camera 44 and bottom view camera 46 receive light reflected off objects 22 through a frontal lens assembly 48. The received light is separated by a dichroic prism 50 into its red 52, green 54, and blue 56 components. The red 52, green 54, and blue 56 components are directed onto a respective one of three charge coupled devices (CCD's) 58, 60, and 62. In addition, an infra-red light source and/or an infra-red sensor may be included, if desired. Each of the charge-coupled devices is preferably a linear array of charge-coupled pixels. Alternatively, the charge-coupled devices could be a two dimensional array. The charge coupled devices 58, 60, and 62 are aligned in three directions, namely, x, y, z, to ensure that corresponding pixels on each charge-coupled device refer to the identical portion of each object 22. Moreover, cameras 44 and 46 are arranged to view their respective sides of all objects 22 simultaneously.

The camera produces an analog signal from each pixel of each charge coupled device 58, 60, and 62 that is proportional to the intensity of light striking the respective pixel. Accordingly, a set of red, blue, and green color signals is produced for each corresponding set of three pixels on the charge coupled devices 58, 60 and 62. A line-by-line image of portions of the objects 22 is obtained as they move past the view of the cameras.

An alternative camera arrangement is three separate linear cameras spaced apart from each other along the direction of travel of the objects 22. Each camera is selected to sense a particular color, namely, red, blue, and green. A time delay between the sensing of each camera is incorporated into the color sorter system to compensate for the time necessary for objects to travel between the cameras. In addition, the system may "flash" on and off the light source (such as the red, blue, and/or green) coupled together with sensing using a monochromatic camera. In this manner, the discrimination of defects may be improved.

It is to be understood that any number and type of camera system may be employed to obtain multiple color images of at least a portion of one or more objects to be sorted or otherwise classified. The number, type, and range of colors is selected so as to be suitable for the particular objects and subsequent signal processing employed. The colors may include any wavelength, such as x-ray, ultraviolet light, and infrared, and ay selection of one or more colors.

Referring again to FIG. 1, a top main light 63 and a bottom main light 65 include a florescent or quartz-halogen lamp to illuminate respective sides of the objects 22 imaged by the cameras 44 and 46. A bottom view background 64 and a top view background 66 are aligned within the viewing area of the respective cameras 44 and 46, so that the light detected in regions between the objects 22 has a known intensity and color. Such intensity and color are adjusted so that the reflections from the backgrounds 64 and 66 match the intensity and color of light reflected from an acceptable product or object. Accordingly, the light received from regions between adjacent objects is interpreted as acceptable objects. Otherwise, the sorter system 16 may interpret the regions between adjacent objects as unacceptable objects.

Figure 3:
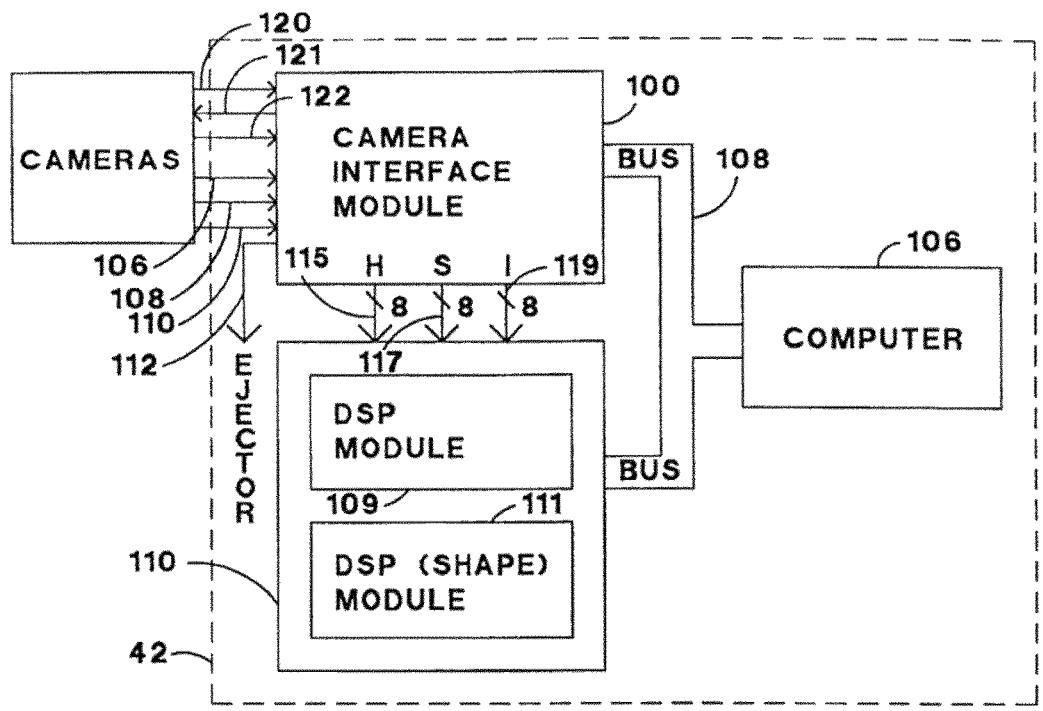
FIG. 3 is a block diagram of the electronics of FIG. 1 including a camera interface module.

Referring to FIG. 3, the electronics 42 include a camera interface module 100 which processes the color signals from the cameras. One or more cameras may interface with the camera interface module 100. Each camera transmits red 106, blue 108, and green 110 color signals to the camera interface module 100. The cameras and camera interface module 100 communicate with each other via a valid video in 120, start 121, and clock out 122. Each of the color signals 106, 108, and 110 are preferably analog in nature and transmitted on a separate line. However, the color signals 106, 108, and 110 may be in any other form, such as digital, or combined together in one or more composite signals. The color signals could be transmitted from the cameras to the electronics 42 by other methods, such as for example, mechanical, optical, or a radio transmitter-receiver.

The camera interface module 100 is controlled by a computer 106 via a bus 108. A digital signal processor module 110 has one or more digital signal processors 109, and 111 to provide added signal processing capabilities, if necessary. For example, such signal processing may include determining the density, shape, and size of objects. The camera interface module 100 is interconnected with the digital signal processor module 110 with three lines, namely, a hue line 115, a saturation line 117, and an intensity line 119. One or more control lines 112 interconnect the camera interface module 100 and the ejector manifold 38 to sort objects 22.

Figure 4:
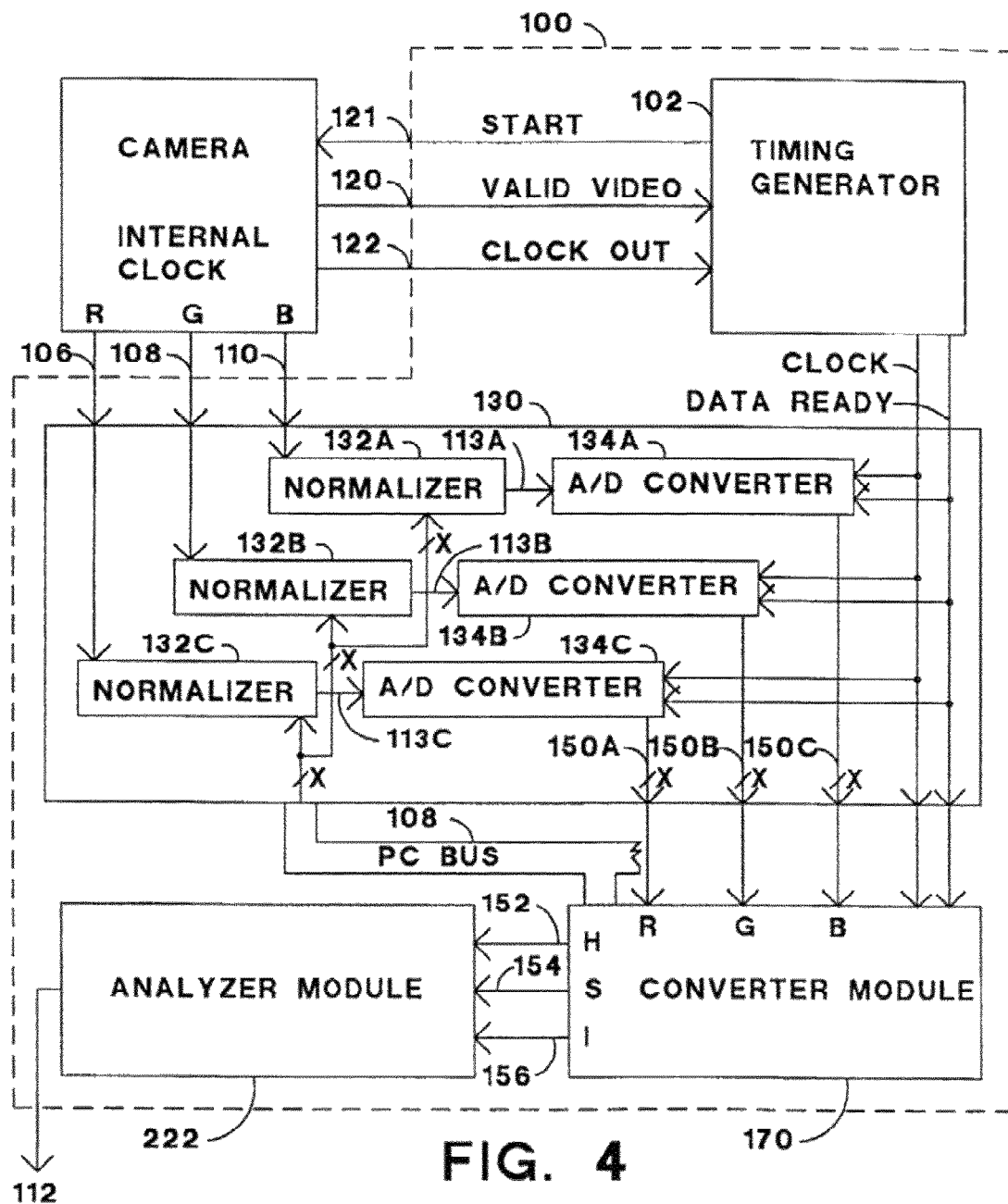
FIG. 4 is a block diagram of the camera interface module of FIG. 3, including a normalizer, a converter, and an analyzer.

Referring to FIG. 4, the camera interface module 100 includes a timing generator (TG) module 102. The TG module 102 initiates a camera scan via the start signal 121. The camera(s) in turn respond by returning a valid video signal 120, a synchronizing clock output 122 and three video signals, red 106, green 108, and blue 110. The TG module 102 controls when the sensing of objects is done, and the transmission of color signals from the camera to the camera interface module 100.

Figure 5:
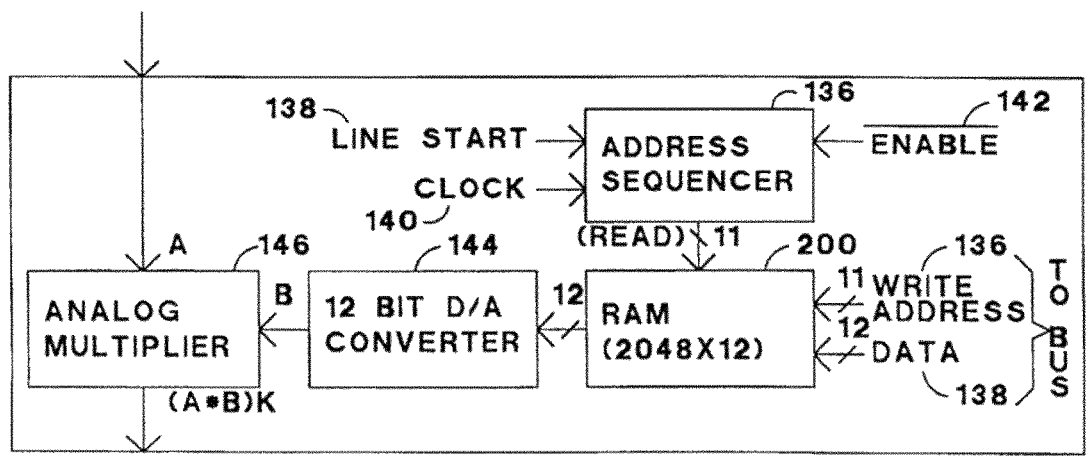
FIG. 5 is a block diagram of the normalizer of FIG. 4.

The red 106, green 108, and blue 110 color signals from each of the cameras 44 and 46 are transmitted to an analog-to-digital converter (A/D) module 130. The A/D module 130 includes three normalizers 132a, 132b, 132c to normalize each of the color signals and three analog-to-digital converters 134a, 134b, 134c to convert the normalized analog color signals to a digital format. The cameras view objects from a central location across a relatively wide view which results in light intensity variations in the observed light. The normalizers 132a-132c are designed to compensate for light intensity variations across the view of the camera in a conventional manner. Referring to FIG. 5, each normalizer 132a-132c receives a respective analog input signal representative of a particular color. A random access memory (RAM) 200, preferably 2048×12, is addressed by the computer 106, via the bus 108, with write address lines 136 and data lines 138 to load compensation data into the RAM 200. The compensation data is representative of the gain necessary to compensate each pixel for anticipated light intensity variations. An address sequencer 136 is controlled by a line start signal 138, clock signal 140, and enable signal (active low) 142 to address the data within the RAM 200 corresponding to the respective analog signal currently being transmitted to the normalizer. The analog color signals are sequentially transmitted to the normalizer by the camera so the gain compensation data is likewise addressed in a sequential manner. The RAM 200 transmits digital data to a digital-to-analog converter 144 which produces a corresponding analog output signal. The analog output of the digital-to-analog convertor 144 and the analog color signal received by the normalizer are multiplied together by an analog multiplier 146. The output of the analog multiplier 146 is transmitted to a respective A/D converter 134a-134c. The outputs 150a-150c of the analog-to-digital converters 134a-134c are inputs to the converter module 170. In summary, each normalizer multiplies the analog color signals of each pixel by a particular gain factor for that pixel determined during calibration. Each normalizer circuit 132a-132c is identical except for different compensation data, if necessary. The timing for the addressing of the address sequencer 136 is controlled from the TG module 102.

To make the system more insensitive to light intensity variations the color signals may be transformed by the convertor 170 to a different color space, such as a hue signal 152, a saturation signal 154, and an intensity signal 156. The combination of the hue, saturation, and intensity is known conventionally as a HSI model. The HSI model may also be known as hue-saturation-luminescence model, hue-saturation-brightness model, hue-saturation-value model, etc. In general, the HSI model is based on the intuitive appeal of the "hue", which is a definition of the actual color, such as red, orange, yellow, blue-green, etc. The "saturation" is a definition of how pure the color is, and may be considered a measure of how densely the hue is spread on a white background. The "intensity" is a definition of the amount of light reflected from an object. The HSI color space model, as opposed to the red-green-blue model, relates more closely to the colors of human perception so that operator adjustments are more intuitive.

Figure 6A:
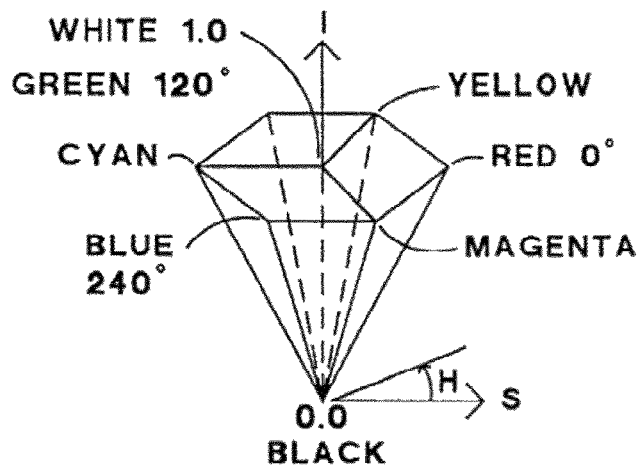
FIGS. 6A and 6B are diagrams of the converter of FIG. 4.
Figure 6B:
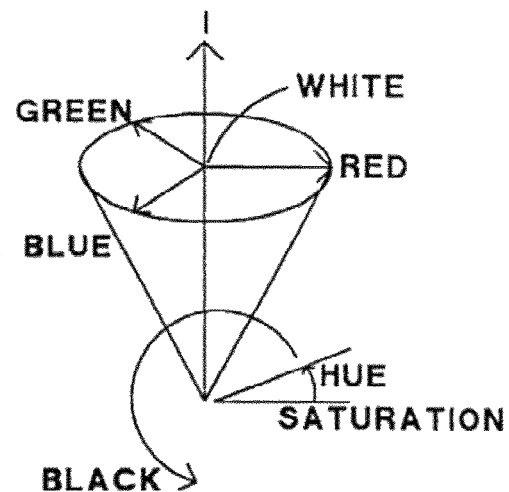

Referring to FIGS. 6A and 6B, representation of the HSI model can be a cylindrical coordinate system, and the subset of the space within which the model is defined as a cone, or circled pyramid. The top of the cone corresponds to I=1, which contains the relatively bright colors. The colors of the I=1 plane are not all the same perceived brightness, however. The hue H is measured by the angle around the vertical axis, with red at 0°, green at 120°, and so on. Complementary colors in the HSI circle are 180° opposite one another. The value of saturation S is a ratio ranging from 0 on the center line I axis to 1 on the triangular sides of the cone. Saturation is measured relative to the color gamut represented by the model, which is a subset of the entire CIE chromaticity diagram. Therefore, saturation of 100 percent in the model is less than 100 percent excitation purity.

The cone is one unit high in I, with the apex at the origin. The point at the apex is black and has an I coordinate of 0. At this point, the values of H and S are irrelevant. The point S=0, I=1 is white. Intermediate values of I for S=0 on the center line are the grays. When S=0, the value of H is irrelevant (called by convention UNDEFINED). When S is not zero, H is relevant. For example, pure red is at H=0, S=1, I=1. Indeed, any color with I=1, S=1 is akin to an artist's pure pigment used as the starting point in mixing colors. Adding white pigment corresponds to decreasing S without changing I. Shades are created by keeping S constant and decreasing I. Tones are created by decreasing both S and I. Of course, changing H corresponds to selecting the pure pigment with which to start. Thus, H, S, and I correspond to concepts from the artists color system.

Figure 7:
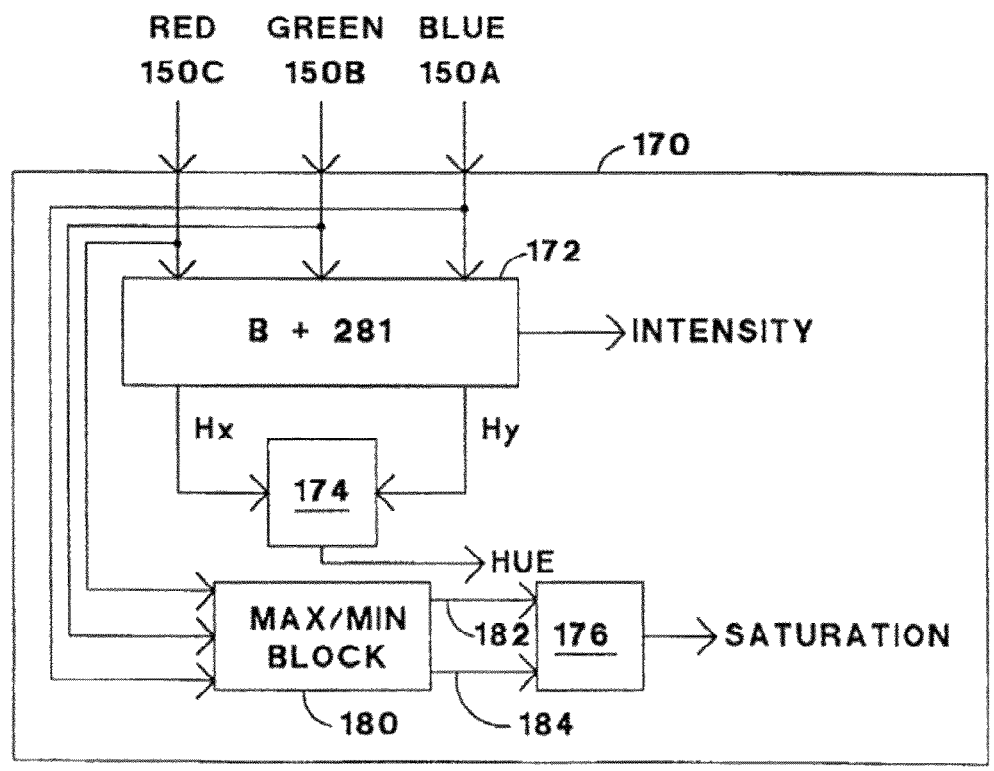
FIG. 7 is a diagrammatic representation of a HSI model space.

Referring to FIG. 7, the converter 170 converts the red 150c, green 150b, and blue 150a color values to a hue 152, a saturation 154, and an intensity 156 value. The converter 170 has three main components, namely, an Integrated Circuit 172, and two look up tables 174 and 176. The tables 174 and 176 include address, data, and control lines (not shown).

Transforming the color signals to a hue range from red to blue (through green) facilitates sorting objects having a wide range of colors. Additionally, by including the capability of obtaining the blue hue from the converter module 170 the saturation and intensity values may be computed. The intensity is a value indicative of the amount of light received and typically does not directly relate to the actual color of the object. Accordingly, the remaining hue and saturation values may be used alone to classify and sort objects. The combination of the hue and saturation values allows greater color recognition, than do hue values alone, in determining whether an object is acceptable or should be rejected.

Figure 8:
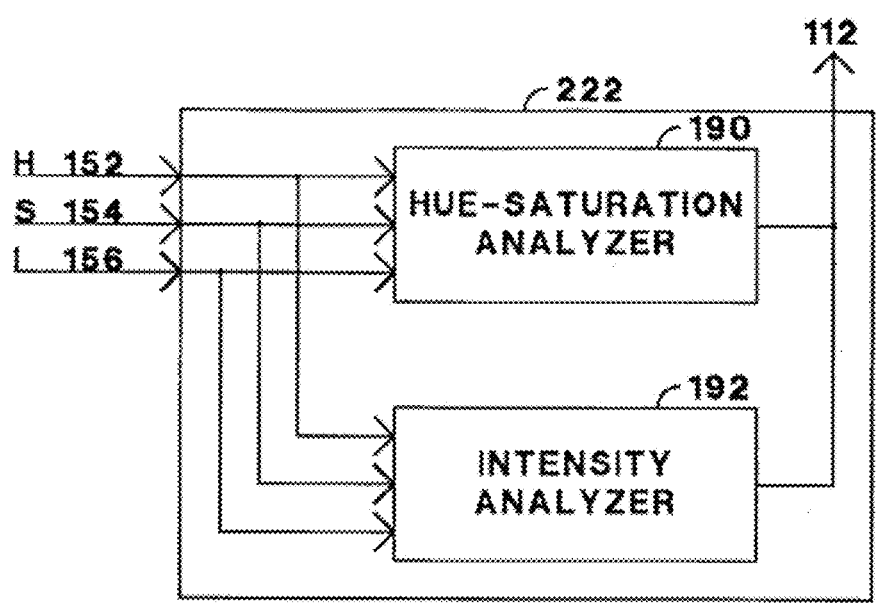
FIG. 8 is a block diagram of the analyzer of FIG. 4.

Referring to FIG. 8, the analyzer module 222 includes two main components, namely, a hue-saturation analyzer 190, and an intensity analyzer 192. The hue-saturation analyzer 190 assigns a unique identification number to each hue and saturation combination. The identification number corresponds to an address in a memory map where data represents either an acceptable object or one that is not acceptable. In response to an unacceptable object a signal 112 is transmitted to the ejector 38 to reject unacceptable objects.

The arctan function used to compute the hue has a range of 90°. However, a color range of 90° is insufficient to properly enhance the colors of objects with different colors. The output of the arctan function has values ranging from −45° to +45°. For convenience, 45° is added to the output to shift the result to values from 0° to 90°. However, both Hx and Hy can be negative, which indicates that a different quadrant should be selected in such case to properly enhance colors. If Hx is negative then the hue should be represented in the next quadrant. Accordingly, 90° is added to the result when Hx is negative so that the next quadrant values do not overlap the first quadrant. The result is a range of values from 0° to 180° which automatically enhances the appropriate colors. The 0 to 180 degree range is scaled to a 0 to 240 degree range to accommodate an 8 bit system. The remaining values from 241 to 256 are reserved for control and error checking functions.

The analyzer includes an intensity module 192. When the color values are such that red=green=blue, the saturation and hue are both undefined corresponding to a shade of gray. Also, as the saturation value approaches zero it becomes increasingly undefined and is not a reliable indicator to use in sorting. Accordingly, a threshold value is incorporated into the intensity module 172 which triggers the use of the threshold module 172 when the saturation value or the difference between two or three of the colors is lower than a threshold value. When this condition occurs, the intensity value is used, as opposed to the hue and saturation, to determine if the product is acceptable or should be rejected. Thus, the intensity module 172 accounts for those conditions when the data is undefined or unreliable.

Figure 9:
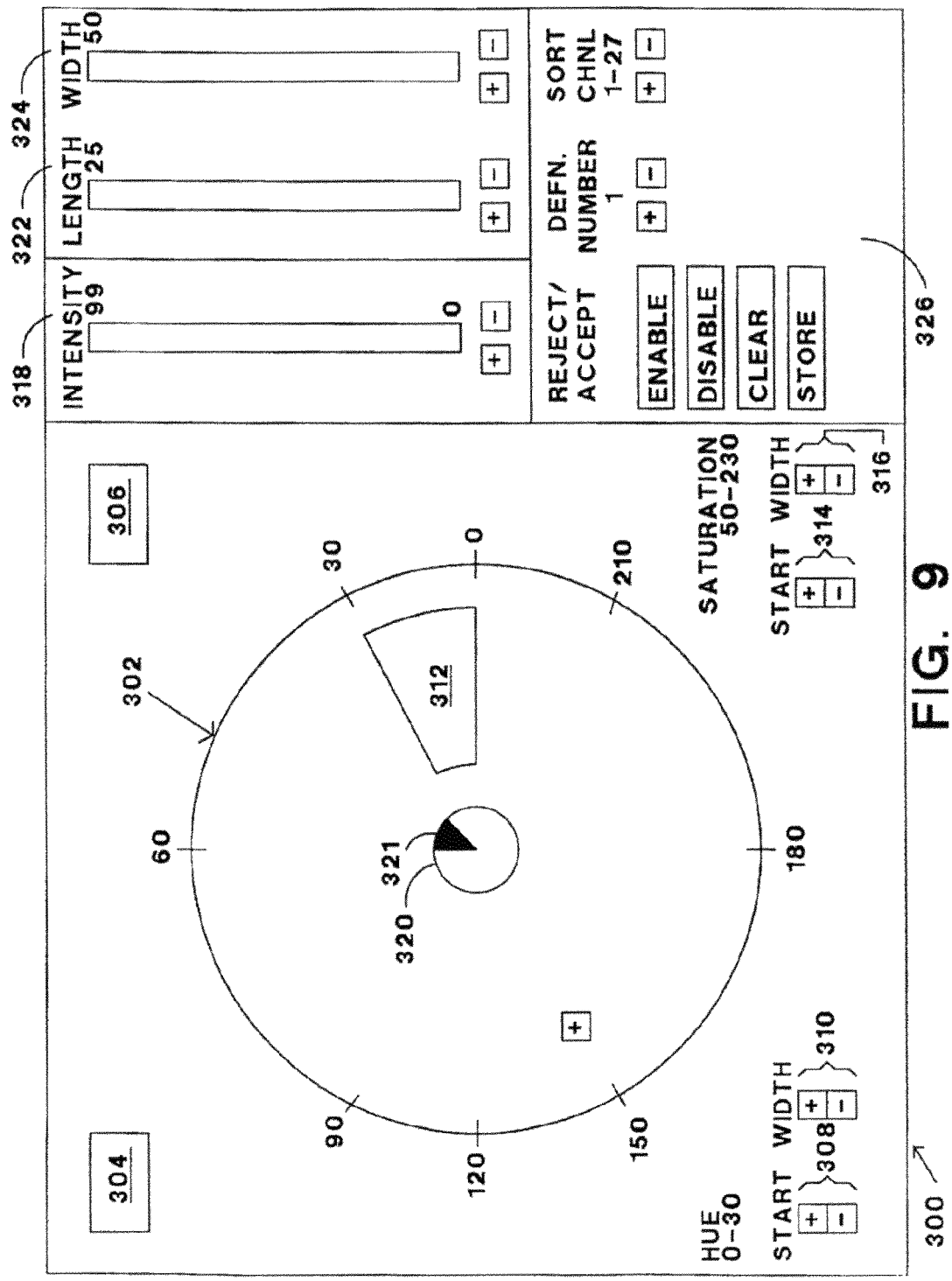
FIG. 9 is an illustrative diagram of an operator display.

Referring to FIG. 9 the operator display 300 includes a graphical representation of the hue, saturation, and intensity classification criteria for objects. The display 300 includes a color wheel 302 which defines acceptable or rejectable hue values in an angular manner around the color wheel, with values between 0 and 240. The color wheel 302 defines acceptable or rejectable saturation values as distances along a radii of the color wheel 302. A hue of 0 is a red color, a hue of 80 is a green color, and a hue of 160 is a blue color. By selecting the define accept button 304 or define reject button 306 the operator can select whether regions defined on the color wheel 302 indicate acceptable or objects to be rejected, respectively. The start buttons 308 and width buttons 310 are used to define the hue range (arc on the color wheel 302) of a region 312. The start buttons 314 and width buttons 316 are used to define the saturation range (distances on the radii of the color wheel) of the region 312. Additional regions may be defined on the color wheel 302 to indicate additional acceptable or reject objects. The threshold value for the intensity sorting criteria is selected with the intensity selector 318. The value selected by the intensity selector 318 is illustrated on the color wheel 302 as the diameter of a central circular region 320. When the central region 320 is selected, the start buttons 308 and width buttons 310 are used to select the acceptable shades of grey as indicated by the darkened area 321 within the central region. In addition a length selector 322 and width selector 324 may be used to further define the width and length required for acceptable or rejectable objects within one or more regions 312. The control section 326 is used to store, retrieve, disable, and enable different predefined patterns on the color wheel 302. Further, a set of patterns can be used for multiple lanes (sort channels) of products in order allow simultaneous sorting of multiple different types of objects, each with a different classification criteria. The color sorter also includes a capture facility whereby an image of an object can be captured on the display and its color content displayed on the color wheel to assist the operator in defining that object as acceptable or rejectable. As illustrated, the system includes the capability of discriminating regions of hue and saturation for sorting. In addition, the system includes the capability of discriminating grey levels, as indicated by the darkened area 321, for sorting.

Figure 10:
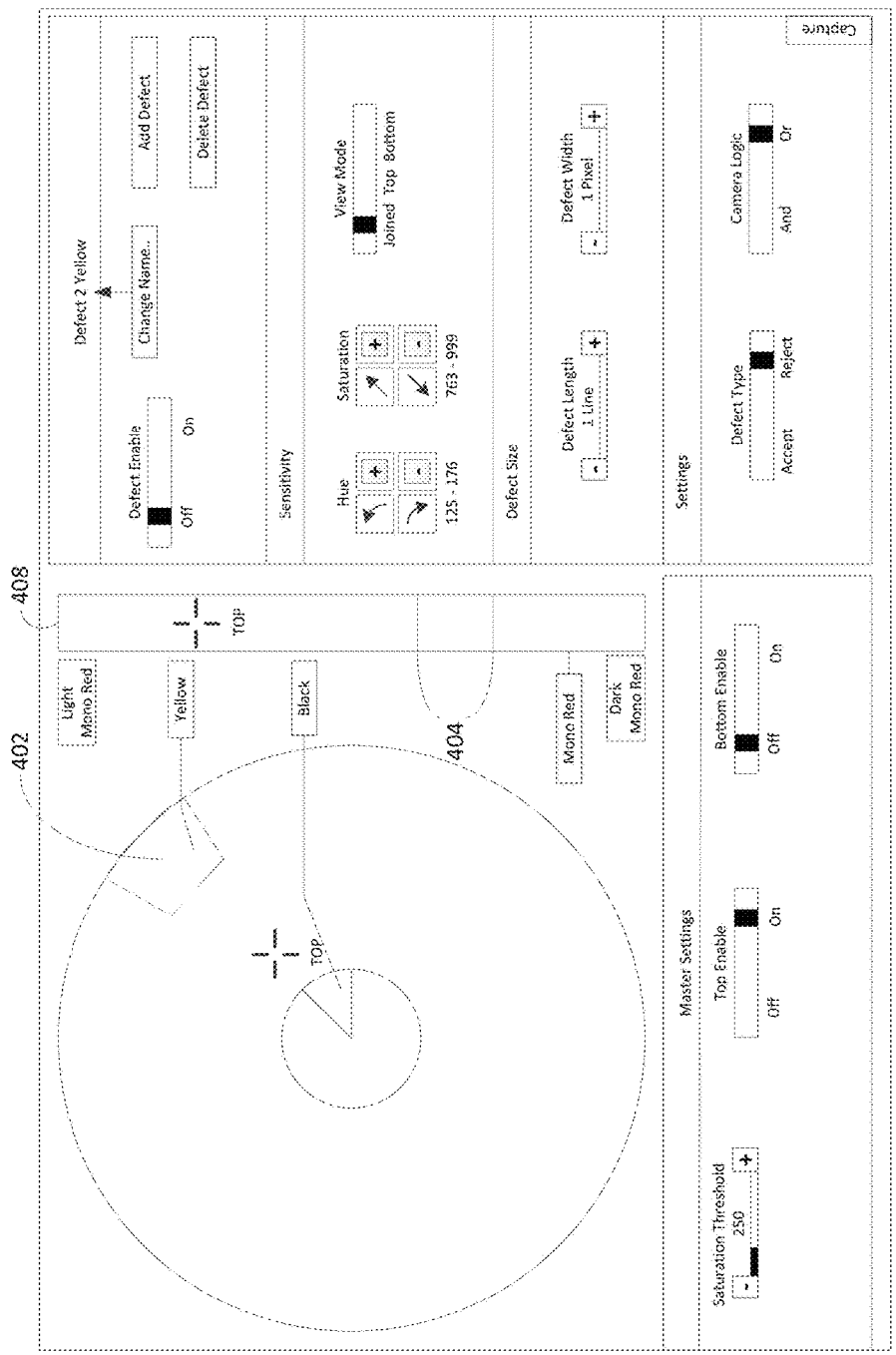
FIG. 10 illustrates an object discrimination operator display.

Referring to FIG. 10, an operator display 400 may include a graphical representation of the hue, saturation, and intensity classification criteria for objects. With a suitable manipulation of the selection controls, one or more hue and saturation region(s) 402 may be defined for sorting. However, it is difficult using these controls to discriminate objects having particular defect characteristics that are only readily observable under particular lighting characteristics. By way of example, it tends to be difficult to distinguish defects in a product with minimal color differences when viewed under white light (e.g., a broad spectrum of red, blue, and green) but may also tend to have readily identifiable intensity defects that are identifiable under a particular color light (e.g., generally green spectrum of light). To facilitate an improved defect discrimination, it was determined that in addition to the selection of the range of hue colors (e.g., an arc on the color wheel), and the selection of the range of saturation colors (e.g., a radius on the color wheel), it is desirable to further include the capability of discriminating based upon a threshold related to a monochromatic color. Monochromatic colors are all the colors, (e.g., tints, tones, and shades) of a single hue. Monochromatic colors may be derived from a single base hue and extended using its shades, tones and tints. Tints may be achieved by adding white, and shades and tones may be achieved by adding a darker color, gray or black. The range of the monochromatic color may be selected by using a pair of sliders 404 on a rectangular region 408 to select a range of the monochromatic color to be used for object discrimination. By way of example, the monochromatic color may be selected to be red, the monochromatic color may be selected to be green, or the monochromatic color may be selected to be blue. Moreover, the range may be selected with a single slider using either the maximum or the minimum as the other extent of the range. In this manner, the defect is selected based upon a combination of the hue, saturation, grey scale, and/or monochromatic color.

It is difficult to accurately determine the optimal settings for a particular product by modifying the defect settings, and inspecting the rejected products and the non-rejected products, in light of the modified defect settings. This process of testing products (e.g., modify defect settings, inspect products, modify defect settings, inspect products) is repeated until a sufficiently accurate setting is achieved. In addition to being burdensome to perform this inspection adjustment process, the operator does not know whether more optimal settings may be achieved without further modifications of a multitude of different potential settings, such as for example, the hue, the saturation, the grey levels, etc.

Figure 11:
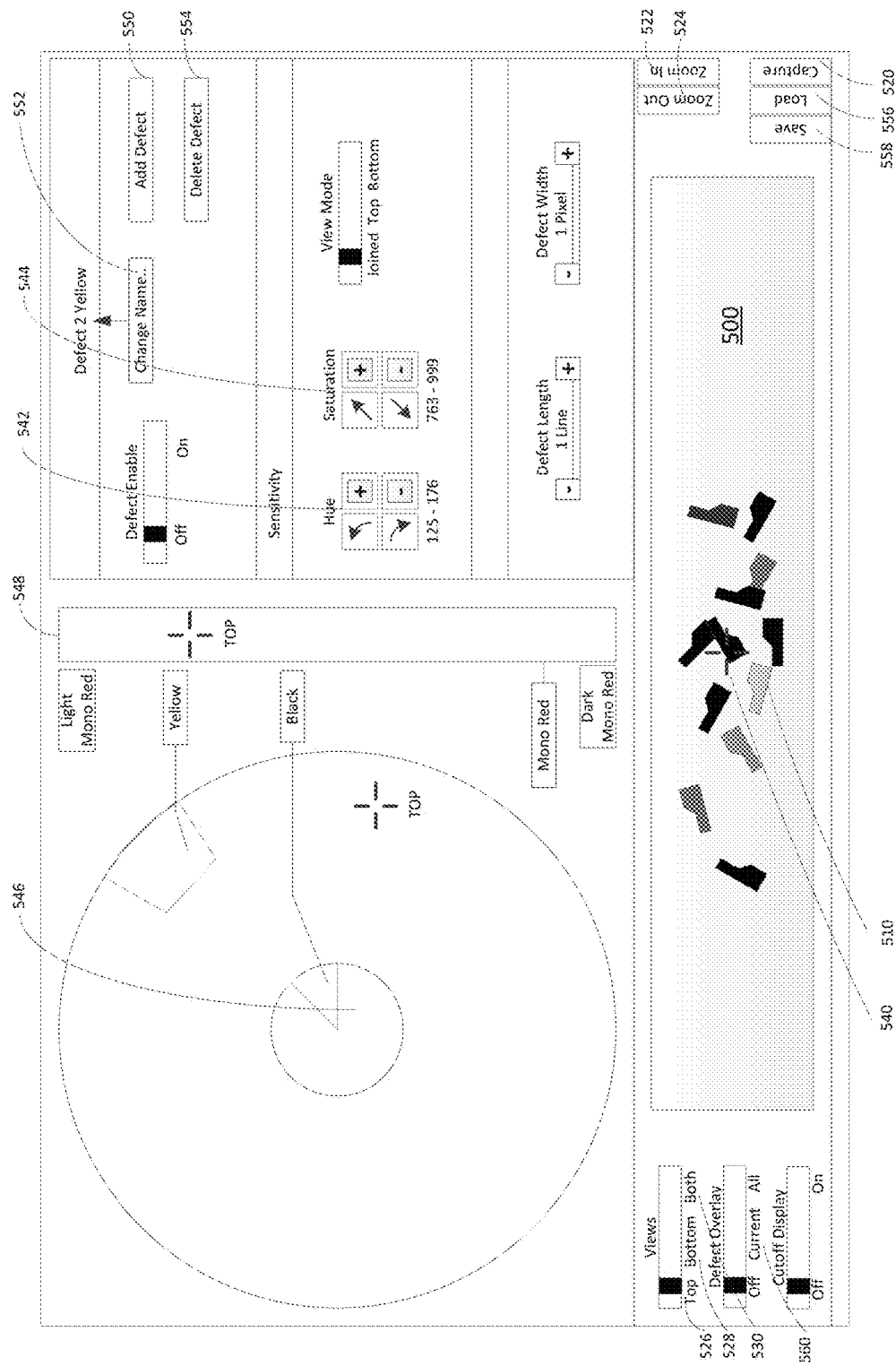
FIG. 11 illustrates another object discrimination operator display.

Referring to FIG. 11, it is desirable to capture an image 500 of an exemplary set of products 510 that are to be sorted. The operator may select to add a defect to the process by capturing an image 500 (e.g., capture option 520) of the products to be sorted. The captured image 500 may be zoomed in 522, zoomed out 524, the top camera(s) may be selected 526, the bottom camera(s) may be selected 528, and both the top and bottom camera(s) may be selected 530. A set of cross hairs 540 may be moved on the captured image 500 to identify a defect in the captured image 500. Once a defect has been identified by the cross hairs 540, the hue 542, the saturation 544, the grey scale 546, and/or monochromatic color characteristics 548 are identified for the corresponding defect on the display for the user to observe.

The user may modify the color characteristics, as desired, and then add the color characteristics as a defect to the system by the "Add Defect" button 550. This process of identifying and adding defects may be continued for other defects in the captured image so that a more complete set of defects are identified. Other options may likewise be included, such as for example, naming of particular defects 552, deleting defects 554, loading images 556, saving images 558, and/or capturing images 520.

Figure 12:
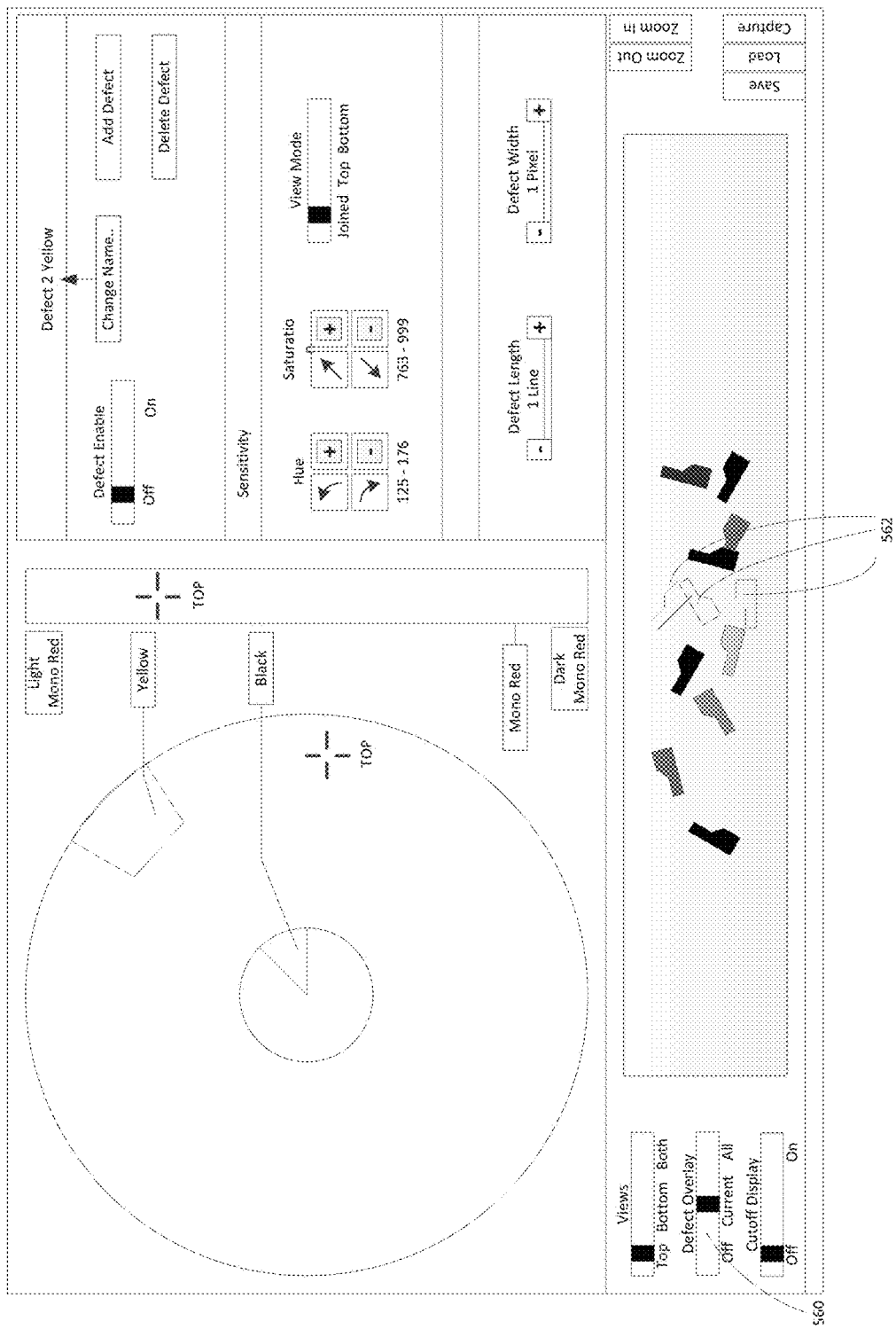
FIG. 12 illustrates another object discrimination operator display.

Referring to FIG. 12, in many cases, it is desirable to graphically observe the effects of the defect identification for which products are likely to be rejected by the system during sorting. An overlay of one or more of the identified defects may be selected (e.g., current defect or all defects 560) and those regions of the image that would be identified as defects are highlighted 562 in some manner. One manner of highlighting is to illustrate the defect regions as "white" which is readily identified with respect to the remainder of the image. This permits the operator to graphically observe the anticipated effects of the rejections for the products. In addition, the operator may change the position of the crosshairs on the color wheel and/or the cross hairs (or otherwise the levels) on the monochromatic color to characterize and add defects.

Figure 13:
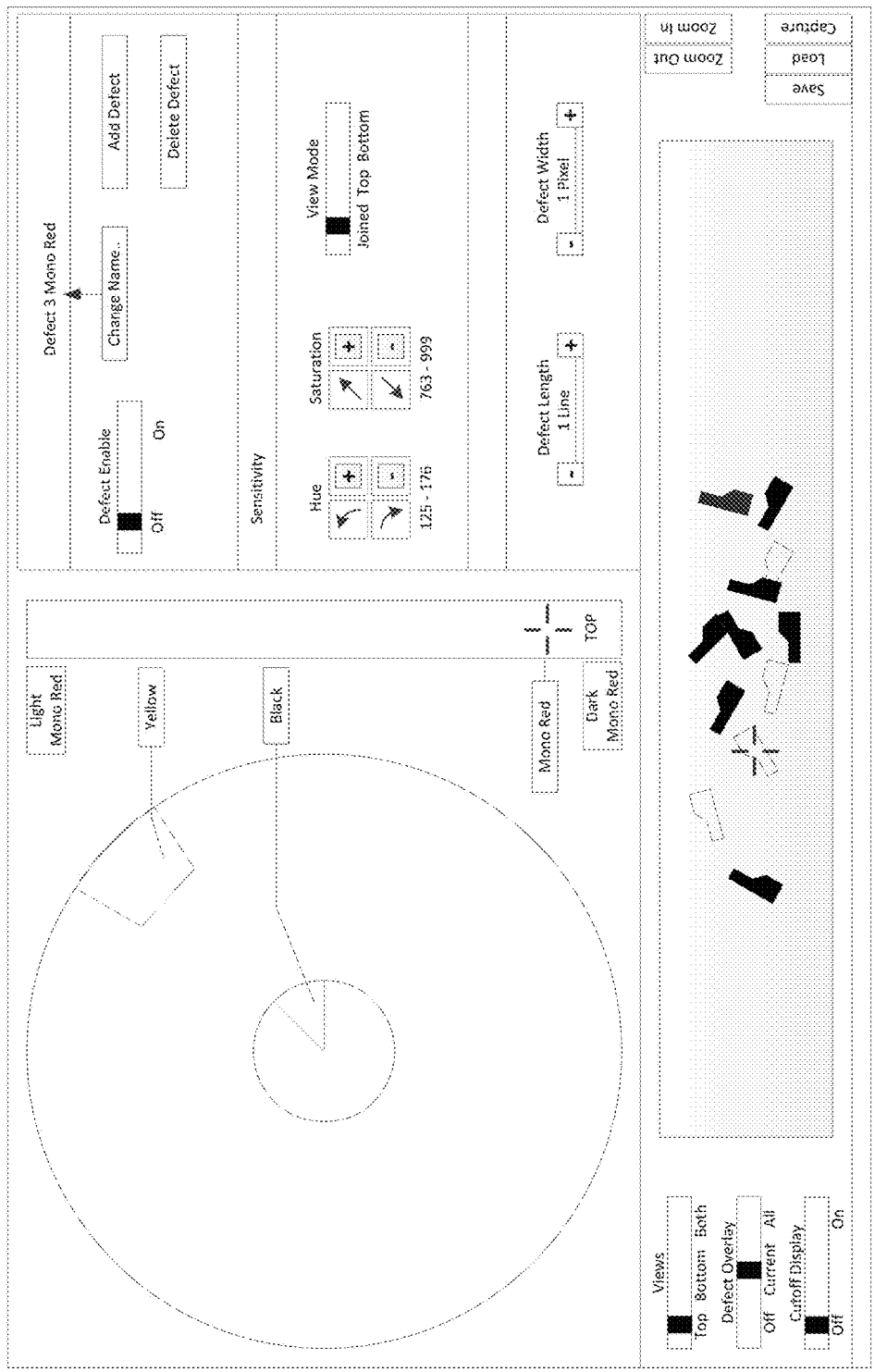
FIG. 13 illustrates another object discrimination operator display.

Referring to FIG. 13, another example is illustrated for the defects being highlighted for a monochromatic red selection. The changes to the defect definition may be observed in "real time" (e.g., without significant delay or other required user interaction) on the display as highlighting of those portions of the products that include the identified defect.

Figure 14:
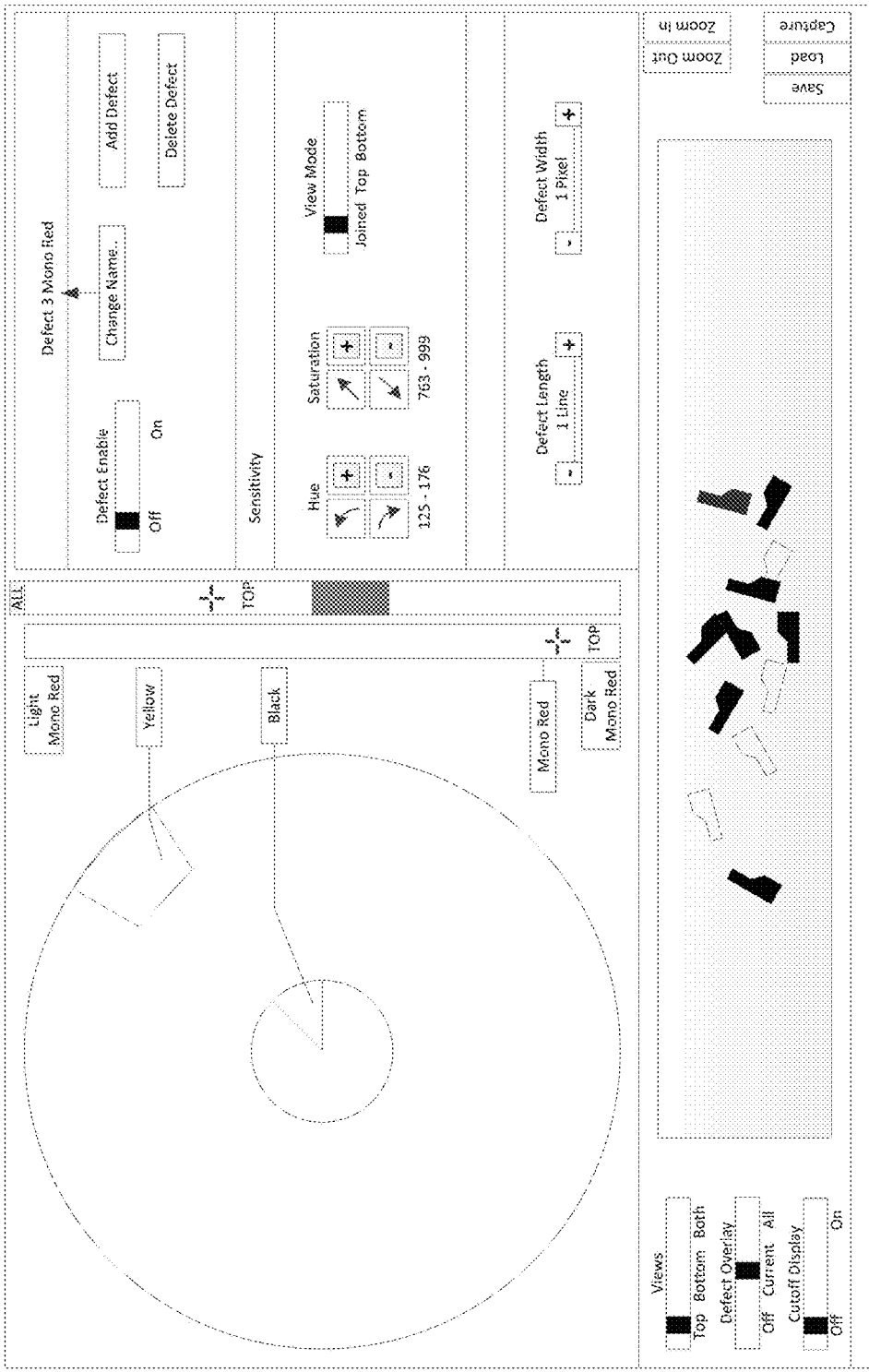
FIG. 14 illustrates another object discrimination operator display.

Referring to FIG. 14, it was determined that in many instances it is difficult using hue, saturation, gray scale, and/or monochromatic controls to discriminate objects having particular defect characteristics that are only readily observable under particular lighting characteristics. By way of example, it tends to be difficult to distinguish defects in some products that tends to be substantially transparent with respect to the visible spectrum of light (e.g., ~400 nm to ~750 nm). By way of example, it also tends to be difficult to distinguish defects in some products that tend to be difficult to distinguish from other objects under the visible spectrum of light (e.g., bones among blanched peanuts and limestone among blanched peanuts). After further consideration, it was determined that such defect materials are distinguishable from non-defect materials using a different and/or supplemental spectrum of light, namely, using near infrared light (e.g., ~750 nm to ~1,100 nm; ~900 nm to ~2,200). For example, the near infrared light may extend over a majority of the range of near infrared light (e.g., ~750 nm to ~1,100 nm), preferably at least 75% of the range of near infrared light (e.g., ~750 nm to ~1,100 nm), preferably at least 50% of the range of near infrared light (e.g., ~750 nm to ~1,100 nm), and preferably at least 25% of the range of near infrared light (e.g., ~750 nm to ~1,100 nm). To facilitate an improved defect discrimination, it was determined that in addition to the selection of the range of hue colors (e.g., an arc on the color wheel), and the selection of the range of saturation colors (e.g., a radius on the color wheel), it is desirable to further include the capability of discriminating based upon a threshold related to a range of infrared light (e.g., a portion of the range of ~750 nm to ~1,100 nm and/or ~900 nm to ~2,200). In addition, one or more sliders may be used to select the range or a selector to identify the entire (or substantially all) of the infrared range. For example, the near infrared light may extend over a majority of the range of near infrared light (e.g., ~900 nm to ~2,200 nm), preferably at least 75% of the range of near infrared light (e.g., ~900 nm to ~2,200 nm), preferably at least 50% of the range of near infrared light (e.g., ~900 nm to ~2,200 nm), and preferably at least 25% of the range of near infrared light (e.g., ~900 nm to ~2,200 nm).

Figure 15:
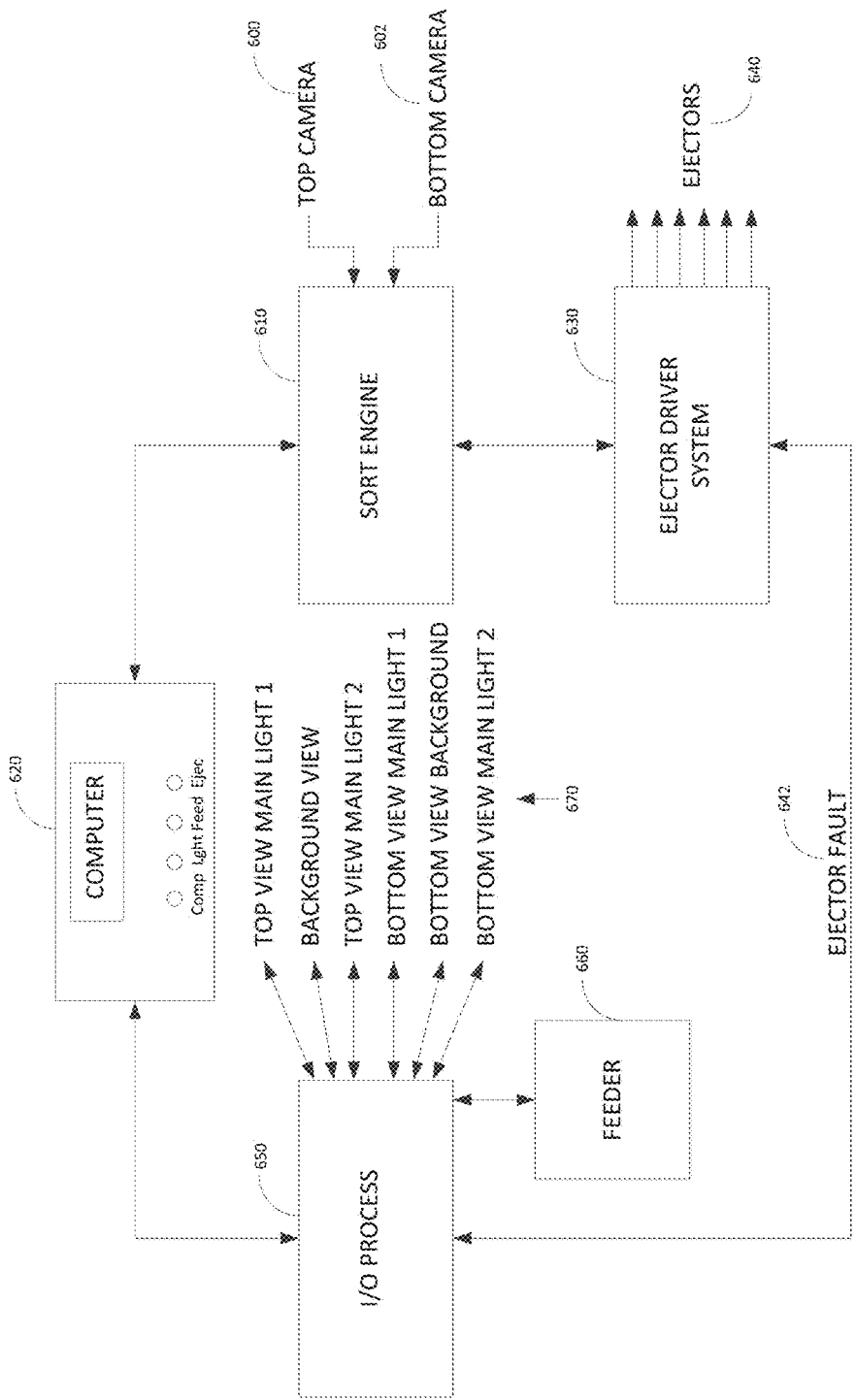
FIG. 15 illustrates a layout of components of a sorting system.

Referring to FIG. 15, the sorting system may include a top camera 600 and a bottom camera 602. The images obtained from the top camera 600 and/or the bottom camera 602 are provided to a sort engine 610. The sort engine 610 determines whether a defect is present in the sensed image(s). The sort engine 610 may be programmed by a computer system 620. The sort engine 610 provides controls to an ejector driver system 630 that triggers the ejectors 640 which sorts the products into those which are acceptable and those which are rejected. If the ejector driver system has a fault, a fault signal 632 is provided to an I/O process 650. The I/O process 650 provides signals to a feeder 660 that control the operation of the feeder 660, such as the speed of the conveyor and the rate at which product is provided onto the conveyor. The I/O process 650 also may provide controls to turn on/off or otherwise adjust the intensity of the top lights and the bottom lights 670. The I/O process 660 is controlled by the computer 620.

Figure 16:
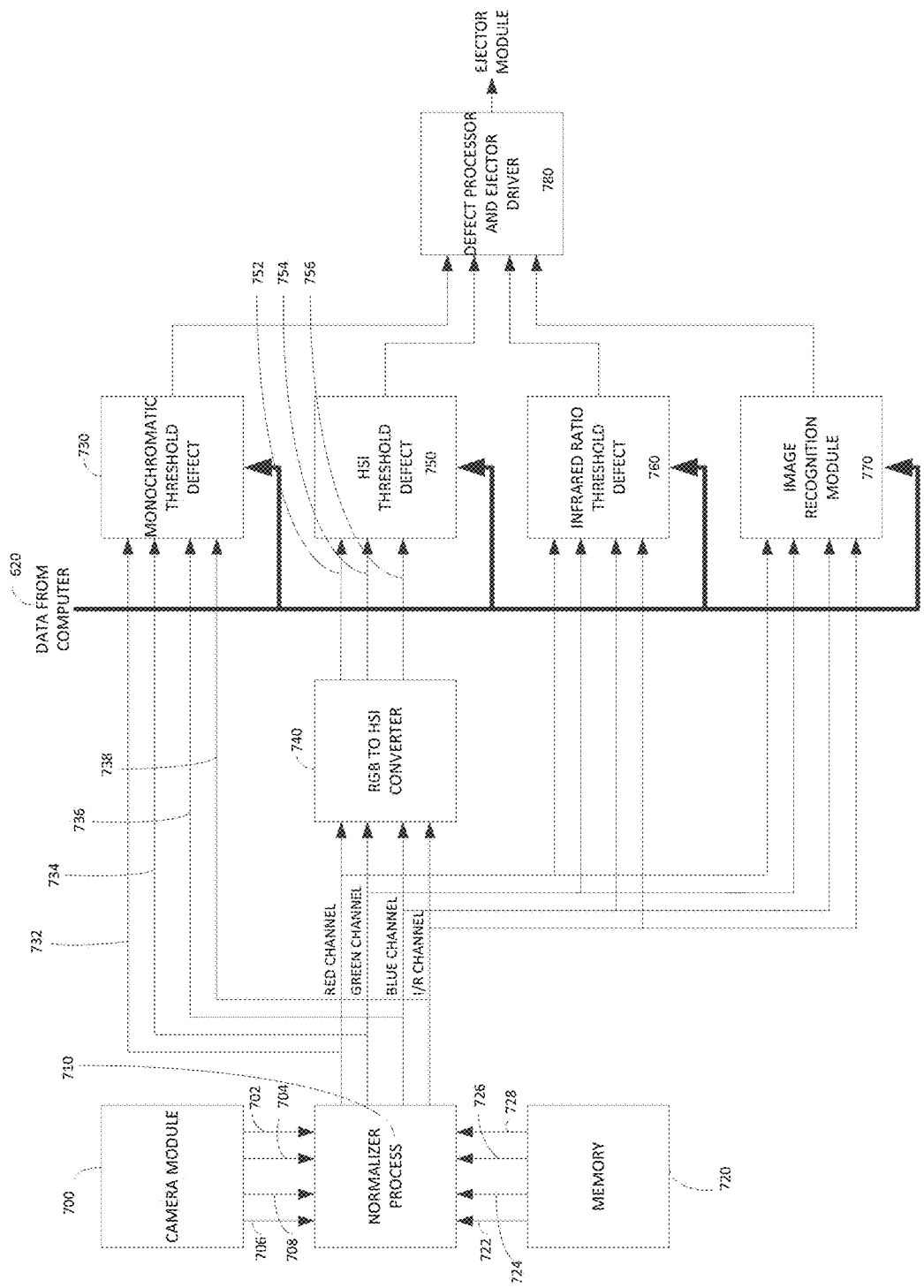
FIG. 16 illustrates another layout of components of a sorting system.

Referring to FIG. 16, the sorting system may include a camera module 700 that includes a red, a green, a blue, and a near infrared camera sensors. The output of the camera module 700 may be a red channel 702, a green channel 704, a blue channel 706, and an infrared channel 708 provided to a normalizer process 710. The normalizer process 710 adjusts for lens and light variations of the particular sorter and the operating environment. The normalizer process 710 may use a memory 720 with corrective data for the normalize process 710 regarding a red channel 722, a green channel 724, a blue channel 726, and an infrared channel 728. The output of the normalizer process 710 may be provided to a monochromatic threshold defect process 730. In particular, the normalizer process 710 may provide a red channel 732, a green channel 734, a blue channel 736, and an infrared channel 738 to the monochromatic threshold defect process 730. The output of the normalizer process 710 may be provided to a RBG to HSI converter 740. In particular, the normalizer process 710 may provide the red channel 732, the green channel 734, and the blue channel 736 to the RGB to HSI converter 740. The output of the RBG to HSI converter 740 may be provided to a HSI Threshold Defect process 750. In particular, the RGB to HSI Converter 740 may provide a hue channel 752, a saturation channel 754, and an intensity channel 756 (e.g., grey scale level) to the HSI Threshold Defect process 750. The output of the normalizer process 710 may be provided to an infrared ratio threshold defects 760. In particular, the normalizer process 710 may provide the red channel 732, the green channel 734, the blue channel 736, and the infrared channel 738 to the infrared ratio threshold defects 760. The output of the normalizer process 710 may be provided to a shape recognition module 770. In particular, the normalizer process 710 may provide the red channel 732, the green channel 734, the blue channel 736, and the infrared channel 738 to the shape recognition module 770. The monochromatic threshold defect process 730, the HSI Threshold Defects process 750, the infrared ratio threshold defects process 760, and/or the shape recognition module process 770 may be provided with information from the computer 620 to indicate the characteristics of the image content to identify as defects. The monochromatic threshold defect process 730, the HSI Threshold Defects process 750, the infrared ratio threshold defects process 760, and/or the shape recognition module process 770 may be provided to a defect processor 780 to identify defects and trigger the ejectors at the appropriate time.

Figure 17:
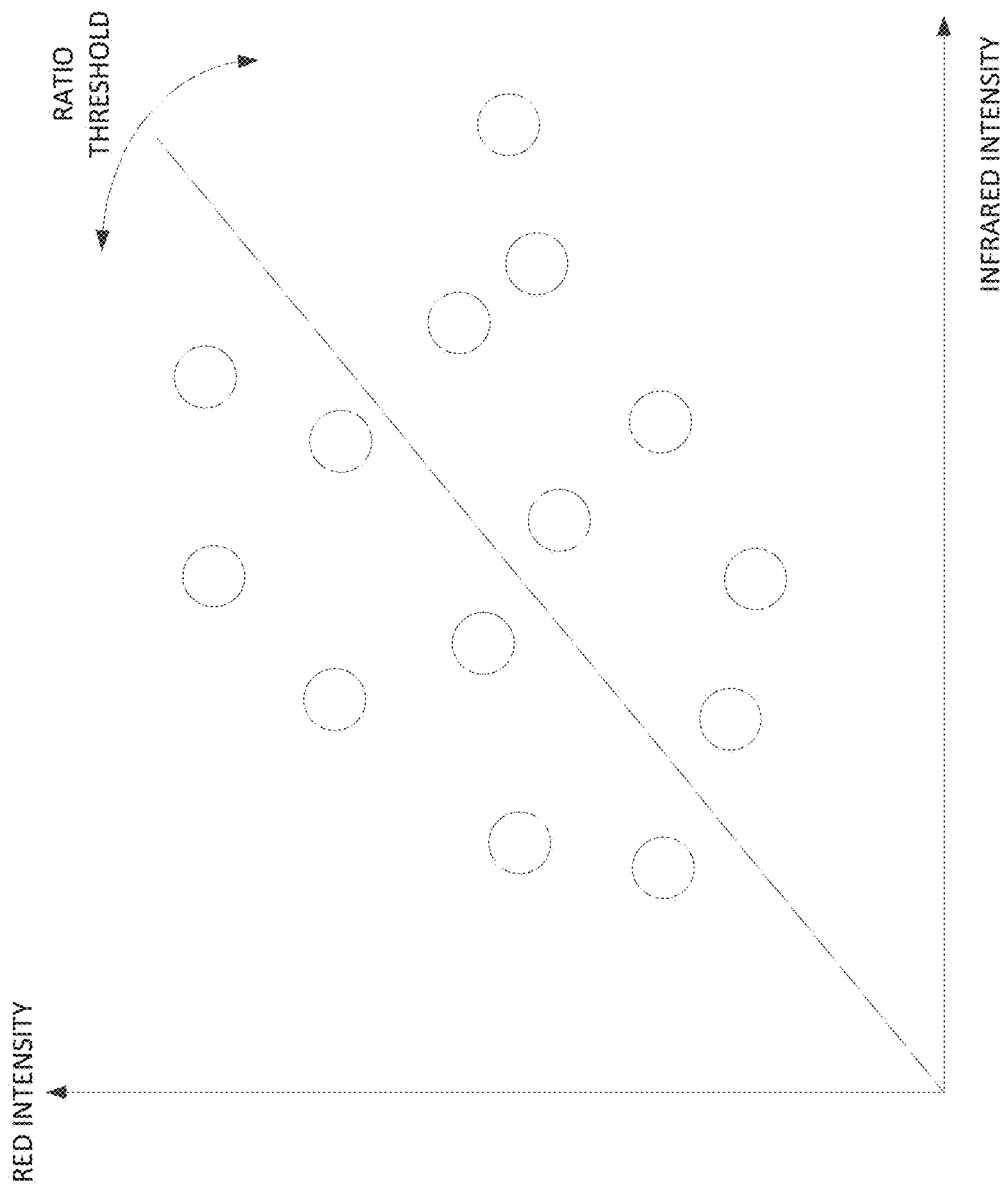
FIG. 17 illustrates an infrared sorting process.

Referring to FIG. 17, the infrared ratio threshold defects process 760 may be based upon a ratio of a monochromatic threshold and an infrared intensity. The infrared intensity data may be processed in a manner similar to the red, blue, and/or green color data, such as for example, comparison to one or more thresholds. In many cases, a defect may be defined as being greater than and/or lesser than a threshold. In the infrared ratio threshold defects process, a two dimensional matrix may be used to identify defects. The X axis may be the infrared intensity while the Y axis may be the monochromatic intensity (e.g., red). A ratio may be selected, such as a linear or non-linear line, to determine products with a defect (e.g., below the line) and products without a defect (e.g., above the line). This infrared ratio threshold defects process provides a measure that facilitates the identifying of defects that are not otherwise readily identifiable.

Figure 18:
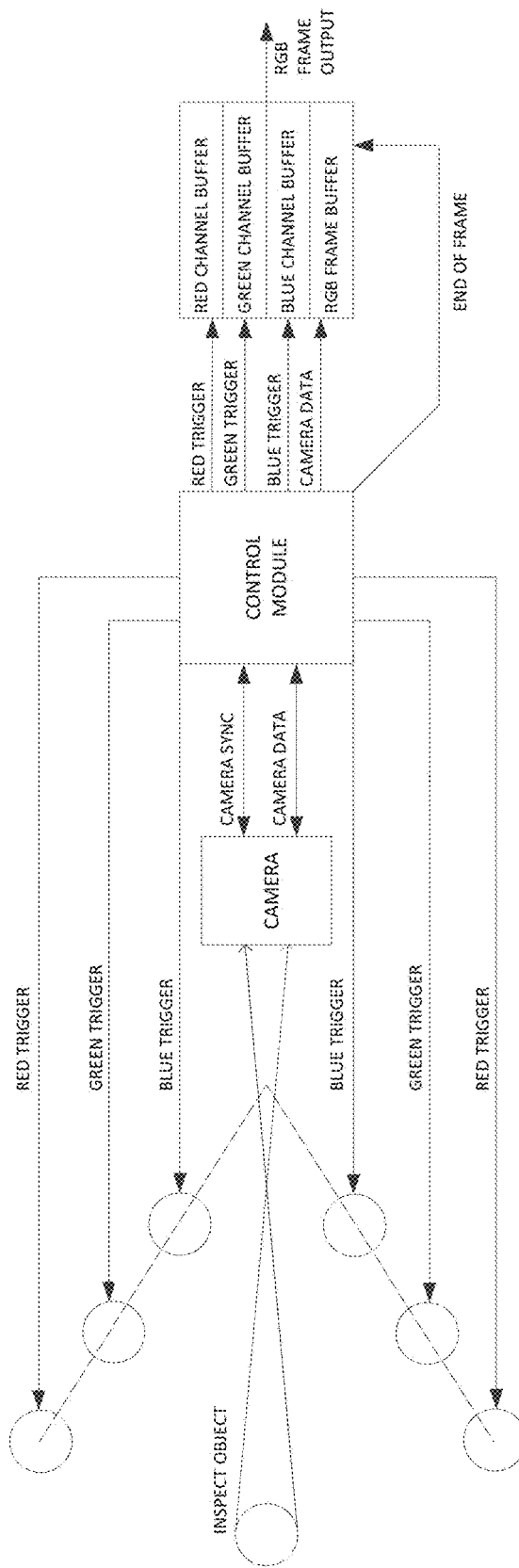
FIG. 18 illustrates an alternative color image acquisition system with multiple colored lights and a monochromatic camera.

Referring to FIG. 18, the preferred system to inspect products includes a monochromatic camera together with multi-colored light sources both of which are synchronized by a control module. The monochromatic camera may include, for example, an area scan camera for a static object or a line scan camera for moving objects. The monochromatic camera may include, for example, either a single or multi photo element (pixels) recording the intensity of the product. The control module may trigger the red light source for the top light source and/or the bottom light source, which is then imaged by the camera. Then the control module may trigger the green light source for the top light source and/or the bottom light source, which is then imaged by the camera. Then the control module may trigger the blue light source for the top light source and/or the bottom light source, which is then imaged by the camera. In this manner, a separate image is obtained for each light source in a sequential manner. Other light sources may likewise be used, as desired. The data obtained by the camera may be provided to the control module, which then provides the captured data to a frame buffer for each of the light colors for a multi-color image. In this manner, the system may "flash" a light source and sense the image with a monochromatic imaging device. The resulting multi-color image (or portions thereof) may be processed by the system to identify defects in the products. The frame buffer may be, for example, a dual port RAM or a rotating buffer. While one side of the RAM (e.g., buffer) is being loaded with camera data, the second port outputs the previously stored red, green, and blue data for further analysis.

The terms and expressions which have been employed in the foregoing specification are used in as terms of description and not of limitation, and there is no intention, in the use of such terms and expressions, of excluding equivalents of the features shown and described or portions thereof, it being recognized that the scope of the invention is defined and limited only by the claims which follow.

I claim:

1. A method of classifying an object comprising the steps of:
   (a) sensing a multiple color image of at least a portion of said object while said object is moving;
   (b) producing color signals from said multiple color image indicative of a plurality of colors in response to sensing said multiple color image;
   (c) transforming said color signals from said multiple color image sensed while said object is moving to (i) a range of hue colors, (ii) a range of saturation colors, (iii) and a monochromatic color signal characterized as all the colors of a single hue; and
(d) variably classifying said object depending upon a combination of (i) a monochromatic threshold related to said monochromatic color signal, (ii) a hue threshold related to said range of hues colors, and (iii) a saturation threshold related to said range of saturation colors.

2. The method of claim 1 wherein said monochromatic color signal extends across the entire range of said monochromatic color.

3. The method of claim 1 wherein a range of said monochromatic color signal is based upon a setting on a graphic user interface.

4. The method of claim 3 wherein said setting is based upon a rectangular region.

5. The method of claim 4 wherein said setting includes a first selector.

6. The method of claim 5 wherein said setting includes a second selector.

7. The method of claim 6 wherein said monochromatic color signal is based upon a range between said first selector and said second selector.

8. The method of claim 1 wherein said monochromatic color is one of red, green, and blue.

9. The method of claim 1 wherein said transforming said color signals from said multiple color image sensed while said object is moving further includes to a hue signal and a saturation signal and said variably classifying said object depending upon a region defined by said hue signal and said saturation signal.

10. The method of claim 1 wherein said multiple color image is sensed as a result of increasing and decreasing the luminance of a light source.

11. The method of claim 10 wherein said increasing and decreasing is turning on and off said light source.

12. A method of classifying an object comprising the steps of:
(a) sensing a multiple color image of at least a portion of said object while said object is moving;
(b) producing color signals from said multiple color image indicative of a plurality of colors in response to sensing said multiple color image;
(c) transforming said color signals from said multiple color image sensed while said object is moving to a monochromatic color signal characterized as all the colors of a single hue, a hue signal, and a saturation signal;
(d) variably classifying said object depending upon a combination of (1) a monochromatic threshold related to said monochromatic color signal and (2) a hue threshold related to a range defined by said hue signal, (3) a saturation threshold related to a range of said saturation signal;
(e) wherein said classification is based upon a graphical interface that displays exemplary objects in a first portion of said graphical interface and displays corresponding range of hue values, range of saturation values, range of monochromatic colors, for a selected portion of one of said objects in said first portion of said graphic interface.

13. The method of claim 12 wherein said graphical interface includes an overlay of said first portion of said graphical interface indicating said classification in real time.

* * * * *

UNITED STATES PATENT AND TRADEMARK OFFICE
CERTIFICATE OF CORRECTION

PATENT NO. : 9,676,004 B2
APPLICATION NO. : 14/934638
DATED : June 13, 2017
INVENTOR(S) : Avi Cohn It is certified that error appears in the above-identified patent and that said Letters Patent is hereby corrected as shown below:

In the Specification

Column 3, Line 30:
Change "ay" to read --any--.

Column 9, Line 26:
Change "sensors" to read --sensor--.

Column 10, Line 50:
Change "are used in as" to read --are used as--.

In the Claims

Column 12, Line 19:
After "signal," insert --and--.

Signed and Sealed this
Seventeenth Day of April, 2018

Andrei Iancu
*Director of the United States Patent and Trademark Office*